(12) United States Patent
Kahn et al.

(10) Patent No.: US 12,002,575 B1
(45) Date of Patent: Jun. 4, 2024

(54) MACHINE LEARNING SYSTEM AND METHOD FOR ATTENDANCE RISK MITIGATION

(71) Applicant: Yale University, New Haven, CT (US)

(72) Inventors: Peter Kahn, New Haven, CT (US); Walter S Mathis, New Haven, CT (US)

(73) Assignee: Yale University

( * ) Notice: Subject to any disclaimer, the term of this patent is extended or adjusted under 35 U.S.C. 154(b) by 0 days.

(21) Appl. No.: 18/360,231

(22) Filed: Jul. 27, 2023

(51) Int. Cl.
  *G16H 40/20* (2018.01)
  *G06Q 10/1093* (2023.01)
  *G16H 10/60* (2018.01)
  *G16H 80/00* (2018.01)

(52) U.S. Cl.
  CPC ......... *G16H 40/20* (2018.01); *G06Q 10/1095* (2013.01); *G16H 10/60* (2018.01); *G16H 80/00* (2018.01)

(58) Field of Classification Search
  CPC ........ G16H 40/20; G16H 10/60; G16H 80/00; G06Q 10/1095
  See application file for complete search history.

(56) References Cited

U.S. PATENT DOCUMENTS

| | | | |
|---|---|---|---|
| 11,309,076 | B2 | 4/2022 | Vegas Santiago |
| 11,380,436 | B2 | 7/2022 | Vegas Santiago |
| 2010/0106517 | A1 | 4/2010 | Kociubinski |
| 2015/0242819 | A1 | 8/2015 | Moses |
| 2018/0174079 | A1 | 6/2018 | Choi |
| 2018/0218337 | A1 | 8/2018 | Polatov |
| 2019/0019163 | A1* | 1/2019 | Batey ............... G16H 50/70 |

(Continued)

FOREIGN PATENT DOCUMENTS

WO  WO-2020016451 A1 *  1/2020  ............. G06N 7/005

OTHER PUBLICATIONS

Daghistani et al., Predictors of Outpatients' No-Show: Big Data Analytics using Apache Spark, 2020, Research Square, pp. 1-22. (Year: 2020).*

(Continued)

*Primary Examiner* — Christopher L Gilligan
(74) *Attorney, Agent, or Firm* — Riverside Law LLP (57) ABSTRACT

A computer-implemented method of increasing appointment attendance comprises providing a processor and a non-transitory memory including computer program code for one or more programs, the memory and the computer program code configured to, with the at least one processor, perform steps comprising obtaining an appointment data structure, comprising an attendee and a corresponding appointment for the attendee, obtaining a set of population data, obtaining a set of appointment data, obtaining a set of external data, obtaining environmental data, inferring, using the population data, the appointment data, the external data, and the environmental data in a machine learning algorithm, a probability that the attendee will attend the appointment, and when the probability of attendance is below a threshold, performing a mitigation step to increase the probability that the attendee will attend the appointment. A system for increasing appointment attendance and a non-transitory computer-readable medium containing computing instructions are also described.

26 Claims, 3 Drawing Sheets

(56) References Cited

U.S. PATENT DOCUMENTS

| | | | |
|---|---|---|---|
| 2020/0151634 A1* | 5/2020 | Cinnor | G06N 20/00 |
| 2020/0160984 A1 | 5/2020 | Vegas Santiago | |
| 2020/0160986 A1 | 5/2020 | Vegas Santiago | |
| 2020/0302358 A1 | 9/2020 | McBride | |
| 2021/0090031 A1* | 3/2021 | Peltz | G06Q 10/1095 |
| 2022/0101986 A1* | 3/2022 | Liu | G06Q 10/1095 |
| 2022/0238215 A1 | 7/2022 | Vegas Santiago | |
| 2022/0277842 A1 | 9/2022 | Ross | |
| 2022/0335339 A1* | 10/2022 | Vegas Santiago | G06N 20/00 |
| 2023/0214784 A1* | 7/2023 | Kakade | G16H 40/20 |
| | | | 705/7.19 |
| 2023/0268062 A1* | 8/2023 | Raghavan | G06Q 10/1095 |
| | | | 705/2 |
| 2023/0282358 A1* | 9/2023 | Shah | G16H 40/20 |
| | | | 705/3 |

OTHER PUBLICATIONS

Liu, D., et al. Machine learning approaches to predicting no-shows in pediatric medical appointment. npj Digit. Med. 5, 50 (2022). 11 pages.

\* cited by examiner

MACHINE LEARNING SYSTEM AND METHOD FOR ATTENDANCE RISK MITIGATION

BACKGROUND OF THE INVENTION

Accurately predicting no-shows to appointments, for example clinical appointments, is of critical importance for healthcare systems and physician offices as slots that are booked and go unused cause serious harm to the business in multiple ways. First, a no-show results in a loss of revenue from the use of the slot. Second, no-show appointments can potentially block or prevent another patient who is on a waiting list from using the slot. Finally, no-show appointments may cause "leakage" of patients into other healthcare systems where they can be seen sooner due to more available slots. While multiple prior efforts have been made to accurately predict no-shows to medical appointments in the outpatient setting, existing models are inaccurate and suffer from insufficient predictive ability. A more complete analysis of this problem may be found in Liu, et al., *npj Digit. Med.*, 2022, incorporated herein by reference.

One deficiency suffered by existing systems attempting to solve this problem is reliance on electronic medical records (EMR) data sources only. Relying on data from within a patient's EMR erroneously assumes that the EMR is sufficiently complete to predict patient behaviors and ignores the reality of the way complex healthcare decisions are made. It also assumes that the EMR is sufficiently robust that it contains enough information to power such a model in all settings and without taking into account other outside variables. Modern technology allows for the measurement and collection of abundant data from a variety of sources which may not at first glance be relevant to the problem at hand. By synthesizing these data and training computational models to make decisions based on the data, a more accurate behavioral model may be developed from which to infer the best course of action for mitigation.

Another deficiency of existing systems is a failure to include economic measures as variables. As noted above, EMRs do not contain measures of economic health that impact patient behavior when they choose to seek care. Such data is not only relevant when considered specifically (e.g. income or housing data related to the patient) but also more generally (e.g. economic health of the general or local economy at the time of the appointment).

Another deficiency of existing systems is a failure to include travel distance, cost, and time. Prior work assumes that all patient journeys to healthcare are equal or not relevant. Unfortunately, patients who live farther away (as calculated either in terms of distance or anticipated travel time) from a clinic or who would incur more significant expense in traveling to the clinic (e.g. gas, tolls, public transportation) are less likely to attend appointments compared to peers who live closer or can travel more cheaply.

Existing systems also lack a nuanced approach to weather models—while some prior models include weather-related variables, none include variables related to visibility, humidity, and other nuanced measures (as opposed to rain vs. shine or absolute temperature).

Finally, no existing system reacts to a poor attendance prediction by taking any mitigatory measures. While attendance prediction may have value by itself, the such a system can truly fill a need if it is able not only to predict when an attendee will likely not attend, but also to choose, based on a variety of factors what if any mitigation strategies might be best implemented at what time prior to the appointment, in order to increase the probability that the attendee attends the appointment.

Thus, there is a need in the art for a more holistic approach to appointment attendance prediction, and, armed with increasingly accurate computational predictive models, mitigation. By doing so, embodiments disclosed herein aim not simply to calculate a probability of a patient attending a given appointment, but to improve overall attendance by taking proactive measures to increase attendance in response to that calculation.

SUMMARY OF THE INVENTION

In one aspect, a computer-implemented method of increasing appointment attendance comprises providing at least one processor; and at least one non-transitory memory including computer program code for one or more programs, the at least one non-transitory memory and the computer program code configured to, with the at least one processor, perform steps comprising obtaining an appointment data structure, comprising an attendee and a corresponding appointment for the attendee, obtaining a set of population data related to the attendee, obtaining a set of appointment data related to the appointment, obtaining a set of external data, obtaining environmental data related to the region around a location of the appointment or the attendee at a designated time, inferring, using the population data, the appointment data, the external data, and the environmental data in a machine learning algorithm by the at least one processor and the at least one non-transitory memory, a probability that the attendee will attend the appointment, and when the probability of attendance is below a threshold, performing a mitigation step to increase the probability that the attendee will attend the appointment.

In one embodiment, the designated time is at least one day prior to a date of the appointment. In one embodiment, the designated time is selected from at least one month prior to the date of the appointment, at least one week prior to the date of the appointment, at least three days prior to the day of the appointment, or at least one day prior to the date of the appointment. In one embodiment, the environmental data comprises weather data. In one embodiment, the external data comprises economic data. In one embodiment, the economic data comprises economic data related to the region around the attendee. In one embodiment, the economic data comprises global or national economic data. In one embodiment, the method further comprises the step of inferring a communication preference of the attendee.

In one embodiment, the mitigation step comprises a communication step selected from written, telephonic, text message, or electronic mail communication based on the inferred communication preference of the attendee. In one embodiment, the mitigation step comprises providing transportation assistance to the attendee, the transportation assistance selected from transportation maps, a ride sharing credit, a public transportation credit, or an ambulance dispatch. In one embodiment, the mitigation step comprises converting the appointment to a virtual appointment or changing a location of the appointment to a home or place of business of the attendee. In one embodiment, the appointment data comprises data selected from a provider of the appointment, a nature of the appointment, whether the appointment is related to a cancer, one or more conditions the attendee holds, one or more diagnoses the attendee is currently being treated for, whether the appointment is telemedicine or in-person, or whether the appointment is an initial consultation or a second opinion.

In one aspect, a computer-implemented method of increasing appointment attendance comprises providing at least one processor; and at least one non-transitory memory including computer program code for one or more programs, the at least one non-transitory memory and the computer program code configured to, with the at least one processor, perform steps comprising obtaining a pending appointment data structure comprising an attendee and a corresponding appointment for the attendee, obtaining a set of electronic medical record (EMR) data related to the attendee, obtaining a set of appointment data related to the appointment, obtaining a set of past appointment data structures, each comprising an attendee identity, a past appointment, and an attendance status of the past appointment, obtaining a set of external data related to the attendees in the set of past appointment data structures, obtaining a set of regional environmental data related to a region around a location of the appointment or the attendees in the set of past appointment data structures from a time of each past appointment, training a machine learning model with the set of past appointment data structures, the set of external data, and the set of environmental data, obtaining environmental data related to the region around the location of the appointment or the attendee in the pending appointment data structure at a designated time, inferring, using the machine learning algorithm, a probability that the attendee will attend the appointment, and when the probability of attendance is below a threshold, performing a mitigation step to increase the probability that each attendee will attend each corresponding appointment.

In one embodiment, the method further comprises the steps of, after the appointment in the pending appointment data structure has passed, recording an attendance status of the attendee at the appointment, and further training the machine learning model with the pending appointment data structure and the attendance status. In one embodiment, the environmental data and the regional environmental data comprise weather data. In one embodiment, the method further comprises the step of inferring whether a mobility factor selected from age, disability status, or travel time is contributive above a predetermined threshold. In one embodiment, the mitigation step comprises providing transportation assistance to the attendee, the transportation assistance selected from transportation maps, a ride sharing credit, a public transportation credit, an ambulance dispatch, or an ambulette dispatch when the mobility factor is above the predetermined threshold. In one embodiment, the attendance status of the past appointment in the appointment data structures is selected from attending, no-show, late, rescheduled, converted to telemedicine, or cancelled surgery.

In one embodiment, the machine learning algorithm is a random forest. In one embodiment, the method further comprises the steps of obtaining the set of EMR data in at least two different data formats, and standardizing the at least two different data formats before training the machine learning model with the EMR data.

In one aspect, a system for increasing appointment attendance comprises a non-transitory computer-readable storage medium with instructions stored thereon, which when executed by a processor, perform steps comprising obtaining an appointment data structure, comprising an attendee and a corresponding appointment for the attendee, obtaining a set of electronic medical record (EMR) data related to the attendee, obtaining a set of data related to the appointment, obtaining a set of external data, obtaining environmental data related to the region around a location of the appointment or the attendee at a designated time, inferring, using the EMR data, data related to the appointment, external data, and environmental data in a machine learning algorithm, a probability that the attendee will attend the appointment, and when the probability of attendance is below a threshold, recommending a mitigation step to increase the probability that the attendee will attend the appointment.

In one embodiment, the instructions further comprise inferring the probability that the attendee will attend the appointment using a trained machine learning algorithm executed on the processor. In one embodiment, the non-transitory computer-readable medium further comprises at least a portion of the database of an EMR system comprising the EMR data. In one embodiment, the instructions further comprise performing the mitigation step, the mitigation step comprising sending one computer-generated electronic communication message to the attendee.

In one aspect, a non-transitory computer-readable storage medium having stored thereon one or more program instructions which, when executed by one or more processors, cause an apparatus to at least perform the following operations: obtain an appointment data structure, comprising an attendee and a corresponding appointment for the attendee, obtain a set of population data related to the attendee, obtain a set of appointment data related to the appointment, obtain a set of external data, obtain environmental data related to the region around a location of the appointment or the attendee at a designated time, infer, using the population data, appointment data, external data, and environmental data in a machine learning algorithm, a probability that the attendee will attend the appointment, and when the probability of attendance is below a threshold, recommending a mitigation step to increase the probability that the attendee will attend the appointment.

In one embodiment, the non-transitory computer readable storage medium further comprises at least one database including at least a subset of the population data, the appointment data, the external data, and the environmental data stored thereon. In one embodiment, the set of population data comprises electronic medical record (EMR) data. In one embodiment, the program instructions are further configured to cause the apparatus to perform at least part of the mitigation step via an automated process.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C #, Objective-C, Java, JavaScript, MATLAB, R, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Figure 1:
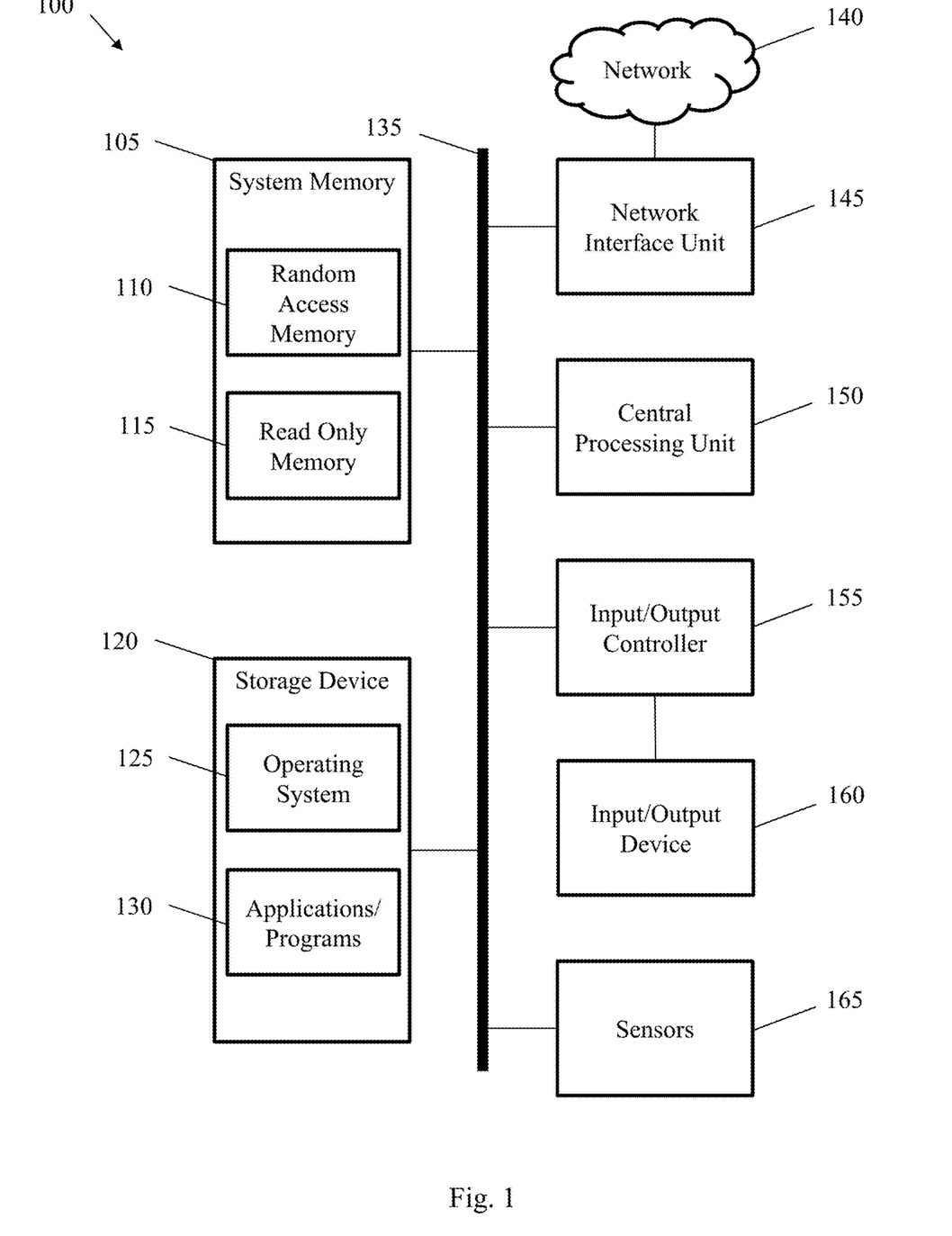
FIG. 1 is an exemplary computing device.

FIG. 1 and the following discussion are intended to provide a brief, general description of a suitable computing environment in which the invention may be implemented. While the invention is described above in the general context of program modules that execute in conjunction with an application program that runs on an operating system on a computer, those skilled in the art will recognize that the invention may also be implemented in combination with other program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

FIG. 1 depicts an illustrative computer architecture for a computer 100 for practicing the various embodiments of the invention. The computer architecture shown in FIG. 1 illustrates a conventional personal computer, including a central processing unit 150 ("CPU"), a system memory 105, including a random access memory 110 ("RAM") and a read-only memory ("ROM") 115, and a system bus 135 that couples the system memory 105 to the CPU 150. A basic input/output system containing the basic routines that help to transfer information between elements within the computer, such as during startup, is stored in the ROM 115. The computer 100 further includes a storage device 120 for storing an operating system 125, application/program 130, and data.

The storage device 120 is connected to the CPU 150 through a storage controller (not shown) connected to the bus 135. The storage device 120 and its associated computer-readable media provide non-volatile storage for the computer 100. Although the description of computer-readable media contained herein refers to a storage device, such as a hard disk or CD-ROM drive, it should be appreciated by those skilled in the art that computer-readable media can be any available media that can be accessed by the computer 100.

By way of example, and not to be limiting, computer-readable media may comprise computer storage media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

According to various embodiments of the invention, the computer 100 may operate in a networked environment using logical connections to remote computers through a network 140, such as TCP/IP network such as the Internet or an intranet. The computer 100 may connect to the network 140 through a network interface unit 145 connected to the bus 135. It should be appreciated that the network interface unit 145 may also be utilized to connect to other types of networks and remote computer systems.

The computer 100 may also include an input/output controller 155 for receiving and processing input from a number of input/output devices 160, including a keyboard, a mouse, a touchscreen, a camera, a microphone, a controller, a joystick, or other type of input device. Similarly, the input/output controller 155 may provide output to a display screen, a printer, a speaker, or other type of output device. The computer 100 can connect to the input/output device 160 via a wired connection including, but not limited to, fiber optic, Ethernet, or copper wire or wireless means including, but not limited to, Wi-Fi, Bluetooth, Near-Field Communication (NFC), infrared, or other suitable wired or wireless connections.

As mentioned briefly above, a number of program modules and data files may be stored in the storage device 120 and/or RAM 110 of the computer 100, including an operating system 125 suitable for controlling the operation of a networked computer. The storage device 120 and RAM 110 may also store one or more applications/programs 130. In particular, the storage device 120 and RAM 110 may store an application/program 130 for providing a variety of functionalities to a user. For instance, the application/program 130 may comprise many types of programs such as a word processing application, a spreadsheet application, a desktop publishing application, a database application, a gaming application, internet browsing application, electronic mail application, messaging application, and the like. According to an embodiment of the present invention, the application/program 130 comprises a multiple functionality software application for providing word processing functionality, slide presentation functionality, spreadsheet functionality, database functionality and the like.

The computer 100 in some embodiments can include a variety of sensors 165 for monitoring the environment surrounding and the environment internal to the computer 100. These sensors 165 can include a Global Positioning System (GPS) sensor, a photosensitive sensor, a gyroscope, a magnetometer, thermometer, a proximity sensor, an accelerometer, a microphone, biometric sensor, barometer, humidity sensor, radiation sensor, or any other suitable sensor.

Attendance Prediction and Mitigation System

In various embodiments, disclosed herein are systems and methods of increasing appointment attendance by a population. Various exemplary embodiments may be described herein related to particular situations, for example patient attendance at a clinical appointment, but it is understood that the systems and methods described herein may be applied equally to any scenario where a fixed number of appointment slots are made available by a "provider" to a population of "attendees." The methods and systems may be considered as a combination of some or all of the following subsystems, described in further detail herein.

As used herein, "appointment" has the following meaning: A commitment in time where two or more people agree to meet either in person, by telephone, by video-conference or by any other means of real-time communication. Examples of an appointment include, but are not limited to, an in-person meeting between two or more persons, an in-person service appointment between one or more service consumers and one or more service providers, a telephone meeting between two or more persons, a video-conference between two or more persons, a web-based conference (video and/or audio) session or other computer-based presentation attended by two or more persons, or any combination of the above.

A first component of the disclosed systems and methods is a data-gathering and processing component, configured to collect data from a variety of data sets to form a master database of information relevant to the population to be considered by the system. A second component of the disclosed systems and methods is a machine learning model, configured to be trained on the data in the master database in order to make inferences based on further data provided to the model. The third and final component of the disclosed system is a mitigation component, configured to suggest mitigation strategies based on the outputs of the trained machined learning model. The system may also be characterized in some embodiments by one or more feedback loops, including the addition of information related to measured conditions at different points in time, mitigation strategies applied, and actual outcomes into the master database for further training of the machine learning model, in order to improve performance in the future.

Data Gathering and Processing

As contemplated herein, a data gathering and processing component may comprise one or more freely available or proprietary databases as well as computer-implemented methods for gathering data from the databases, optionally reformatting some or all data gathered from the databases, optionally combining subsets of the data gathered to form additional, calculated values, and storing data in a centralized or distributed database.

Suitable data sources may include data directly related to appointments, sometimes referred to herein as "appointment data." Data sources may also include data directly related to individuals in, subsets of, or the entire population of possible attendees, sometimes referred to herein as "population data". Data may also include additional data not directly related to appointments, or directly related to the population of possible attendees, sometimes referred to herein as "external data."

One exemplary source of appointment data is time horizon data, particularly the time from when the appointment was made to the actual appointment itself. Time horizon data may be granular and numeric, for example an exact number of minutes, hours, days, weeks, months, etc. between the time the appointment was made and the time of the appointment, or may be gathered and stored as binned data, for example selected from a finite set of groups such as "less than a day," "more than a day but less than a week," "more than a week but less than a month," etc. Time horizon data may also comprise multiple sets of time horizon data, for example if an appointment is made or confirmed on day 0 for day 20 (i.e. 20 days after the day that the appointment is made) but is later postponed by the attendee or by the provider to day 40. The data related to both the original time horizon and the modified time horizon, in addition to which of the attendee or the provider made the change, may be collected separately as separate elements or combined as a single data element related to a single appointment.

Time horizon data may further comprise data about the specific timing of the appointment, regardless of how far in advance the appointment is made—examples include, but are not limited to, the time of day of the appointment, the day of week of the appointment, proximity of the appointment to a time change e.g Daylight Savings Time), the week of year, whether or not the appointment is scheduled on or near a holiday, etc.

Another example of appointment data may comprise factors related to the appointment itself. For example, in some embodiments, particularly in medical appointment applications, the specialty of the clinician, the exact care provider, or the nature of the appointment (e.g. procedure vs. evaluation & management (E&M) services vs. mental health; second opinion vs. initial consultation; cancer related vs. non-cancer; telemedicine vs. in-person; ambulatory procedure vs. invasive surgery, organ system treated) may be included in the appointment data. In some embodiments, appointment data may comprise data related to the number of prior visits to the provider by the attendee and/or the attendee's attendance rate at those prior visits. In some embodiments, appointment data may comprise data related to prior visits to the provider's department, colleagues, and/or institution. In some embodiments, attendance data may comprise a count of how many previous appointments by the attendee at the provider have been converted to telephone or telemedicine appointments. In some embodiments, attendance data may be selected from prior attendance data only of the attendee at the provider in question related to the current appointment being considered. In some embodiments, attendance data may be considered, where available, regarding attendance by the attendee at other provider appointments, and/or attendance by other attendees at the provider of the current appointment.

Population data, as considered herein, may comprise data related to the specific attendee in question, the surrounding population of potential attendees, or one or more subsets of the population of potential attendees at the provider or a pool of providers. In some examples, population data may comprise health factors of the attendee, for example diagnoses given to the attendee by the provider or by other providers, including but not limited to whether or not the attendee has been diagnosed with a cancer or has received a transplanted organ or is immunosuppressed. Population data may further comprise data related to the nature of the disease being treated or diagnosed, including but not limited to Diabetes, Hypertension, Hyperlipidemia, Chronic Obstructive Pulmonary Disease (COPD), Obesity, Cancer of any type, asthma, neuropathy, pain syndromes, depression, anxiety, bipolar disorder, lupus, myositis, chronic kidney disease, cirrhosis, Nonalcoholic Steatohepatitis (NASH), Nonalcoholic Fatty Liver Disease (NAFLD), Primary Biliary Cholangitis (PBC), Immune Thrombocytopenic Purpura (ITP), heart failure, stroke, schizophrenia, developmental delay, dementia, or the like. In some embodiments, the disease or condition being treated may be any disease, disorder, or condition of the musculoskeletal system, speech, sensory system, respiratory system, cardiovascular system, digestive system, genitourinary system, hematological system, skin, endocrine system, neurological system, or immune system. In some embodiments, any condition causing any physical or mental disability that could affect one's ability to physically or logistically attend an appointment may be considered. In some embodiments, population data may comprise data related to whether or not the attendee is a smoker, and/or what degree of a smoker the attendee is, for example a light smoker, heavy smoker, intermittent smoker, etc. In some embodiments, data regarding illicit drug or substance use may be considered as well. In some embodiments, data regarding social determinants of health such as food insecurity, energy poverty, transportation difficulty, housing instability may be considered as well.

Population data may further comprise one or more economic factors. Economic factors may be considered in view of one or more subsets of the population, including but not limited to only the attendee, only a subset of the population geographically surrounding the attendee, only a subset of the population geographically surrounding the provider, only a subset of the population demographically similar to the attendee, etc. In different embodiments, one or more different subsets of the population may be considered in parallel. Examples of economic factors to be considered by a machine learning model of the disclosed system include, but are not limited to, home ownership, cost of house, property tax liability, income tax liability, household and/or individual income, employment status (part time, full time, unemployed, retired), insurance status and payor, vehicle ownership, vehicle registration, liens, bankruptcy, any public statements otherwise available by or about the individual in question, etc. In some embodiments, population data may comprise any and all publicly-available or in some cases proprietary data about the population generally or the attendee specifically. Examples include, but are not limited to, criminal records, psychiatric or medical records, employer, athletic records, news articles, etc.

Population data may further comprise one or more additional demographic factors, including but not limited to gender, sex, race, ethnicity, age, marital status, veteran status, number of children, whether or not the attendee or what subset of the population has disabilities or needs an accommodation, incarceration status of the attendee and/or other members of the household, probation status of the attendee and/or other members of the household, and hospitalization status.

External data, as discussed above, is any data which is not directly related either to the appointment itself or to the population of possible attendees. Examples of external data which may nonetheless be useful in a machine learning model as disclosed herein include, but are not limited to, economic factors, including for example inflation, unemployment rate, and/or the cost of one or more commodities, for example oil and gas. Economic factors may further include cost of food, cost of electricity, cost of heating oil if applicable, local cost of living, local mill rate for real estate taxes, or local income tax rates. In some embodiments, weather factors for the region around the provider and/or the attendee may be considered, for example the high and/or low temperature for the day, approximate temperature at the time of the appointment, relative humidity, wind velocity or direction, cloud cover, precipitation, etc. Additional external factors worth considering may include power outage data where available, emergency management system (EMS)/Fire agency data, traffic pattern data, ride sharing app data (for example whether or not current ride sharing pricing is high due to elevated demand), and/or bus/train/transit data.

The data gathering and processing component may comprise multiple methods and systems for gathering data, including one or more application programming interface (API) connections to third party data sources, website scraping, user surveys, purchased data, etc. The data gathering and processing component may further comprise components configured to clean and/or anonymize, sanitize, or redact received data, and alternatively or additionally data munging or data wrangling, or to manipulate the format and/or values of some or all of the received data in order to standardize the data and make it easier to combine with other sources of data. In some embodiments, the data gathering and processing component may manipulate or combine gathered data to produce additional simplified data for use separately or additionally in various algorithms disclosed herein. For example, month/date/year data may be processed to further compute the day of the week, week of the year, and/or whether or not the appointment falls on or near a holiday. Data related to previous visits may be consolidated into a total number of previous appointments, total number of previous visits, total number of previous no shows, etc. The appointment date and the date the appointment was made may be combined to calculate the days from making the appointment to the appointment. The attendee's home and/or work address and the provider's address may be combined with traffic data and appointment date/time to calculate the travel distance and/or time from the attendee to the provider.

Machine Learning Model

The machine learning model as disclosed herein may in some embodiments be interchangeably referred to as a machine learning algorithm, machine learning engine, or neural network. A machine learning model as contemplated herein may be supervised, unsupervised, or partially supervised. A machine learning model as a component of the system disclosed herein may be trained based on the various data types disclosed herein, for example the appointment data, attendee data, and external data disclosed above and collected for example into one or more databases. The machine learning model may also include in its training results data from past appointments made and attended (or not) by one or more attendees. The machine learning model, once trained, may output a prediction based on the data, in response to an input. The input, in some embodiments, may be a set of data related to one upcoming appointment by one attendee at a provider. The data may be provided to the machine learning model at various points leading up to the time of the appointment, in order to make predictions at multiple time indices. The prediction output from the machine learning model may comprise an estimated probability of attendance by the attendee at the appointment.

In some embodiments, the model may first be trained using a subset of data gathered in one or more master databases, and may be used to make some initial predictions based on that data. The training subset may in various embodiments comprise up to 10% of the data, up to 20% of the data, up to 30% of the data, up to 40% of the data, up to 50% of the data, up to 60% of the data, up to 70% of the data, up to 80% of the data, or up to 90% of the data. The resulting output predictions may then be judged according to one or more binary classifiers, multi-class classifiers, or quality metrics, for example compared against any known appointment attendance data, and the weights of the various data inputs may be refined to maximize the average binary classifiers or quality metrics. In this manner, a machine learning model as disclosed herein can be trained to predict and optimize for any binary classifier or quality metric that can be experimentally measured. Examples of binary classifiers or quality metrics that a neural network can be trained on include but are not limited to show/no-show (e.g. a binary value of whether or not the attendee will show up to the appointment), how late the attendee will be, likelihood that the attendee will request or convert the appointment to a virtual appointment, likelihood that the attendee will request or move the appointment to a different provider, likelihood that the attendee will transfer to a different institution, likelihood of completing visit assignments (e.g. lab work, blood draws, medical imaging, obtaining prescription medications, attending third party rehabilitation sessions, etc.). In some embodiments, quality metrics may include frequency of follow-up visits, medication compliance, health outcomes, or attendee satisfaction ratings. Any other suitable type of quality metric that can be measured. In some embodiments, the machine learning algorithm may have multi-task functionality and allow for simultaneous prediction and refinement of multiple quality metrics.

In some embodiments, the machine learning model may be iteratively updated by retraining the machine learning model using actual results from appointments predicted one way or another by the model, or of any other output metrics as disclosed herein. Updating the machine learning model in this manner may improve the ability of the neural network in inferring one or more outputs, for example attendance probability. For example, in some embodiments, training the machine learning model may include predicting an attendance probability for a set of attendee, appointment, and/or external data related to a particular past appointment, comparing the predicted value to the known result of the appointment, and training the machine learning model based on a result of the comparison. If the predicted value is adequately predictive of the observed value, then the neural network may be minimally updated or not updated at all. If the predicted value differs from the known value, then the neural network may be substantially updated to better correct for this discrepancy.

Although the techniques of the present application are in the context of appointment attendance, it should be appreciated that this is a non-limiting application of these techniques as they can be applied to other types of parameters or attributes. In some embodiments, the machine learning model may have been previously trained using a master data set not available to the user of the machine learning model, and only the trained model is provided to the user. In other embodiments, some or all of the master data set used to train the machine learning model is directly or indirectly available to the user to aid in continuous iterative training.

Examples of specific machine learning algorithms which may be used in the disclosed systems include, but are not limited to, random forest, knearest neighbor (kNN), Support Vector Machines, Artificial Neural Networks, Decision Trees, Boosted Decision Trees, etc.

In various embodiments, a device or system as contemplated herein may be deployed or packaged in different ways. In some embodiments, a system may comprise a software-as-a-service model, wherein the data gathering component and machine learning model are stored in one or more central cloud computing systems or datacenters, and wherein users submit queries to the model remotely, and receive results back. In some embodiments, some or all of the data submitted as a query, and the response, may be used to further train the machine learning model. In other embodiments, a trained machine learning model may be provided to a user for local execution of predictions, for example at the provider site. In these embodiments, some subset of the data used to train the machine learning model may also be provided, or not. In other embodiments, the user is provided with a partially-trained model, and the final training is performed at the user's site and with the user's own data. In one example, a partially trained model may be provided, which was trained to a certain accuracy with generic data, but then that model may be partially or wholly re-trained at the user's site, for example at a provider, by using a subset of a proprietary dataset compiled by the user/provider and pertaining to a population around the user/provider's location.

Figure 2:
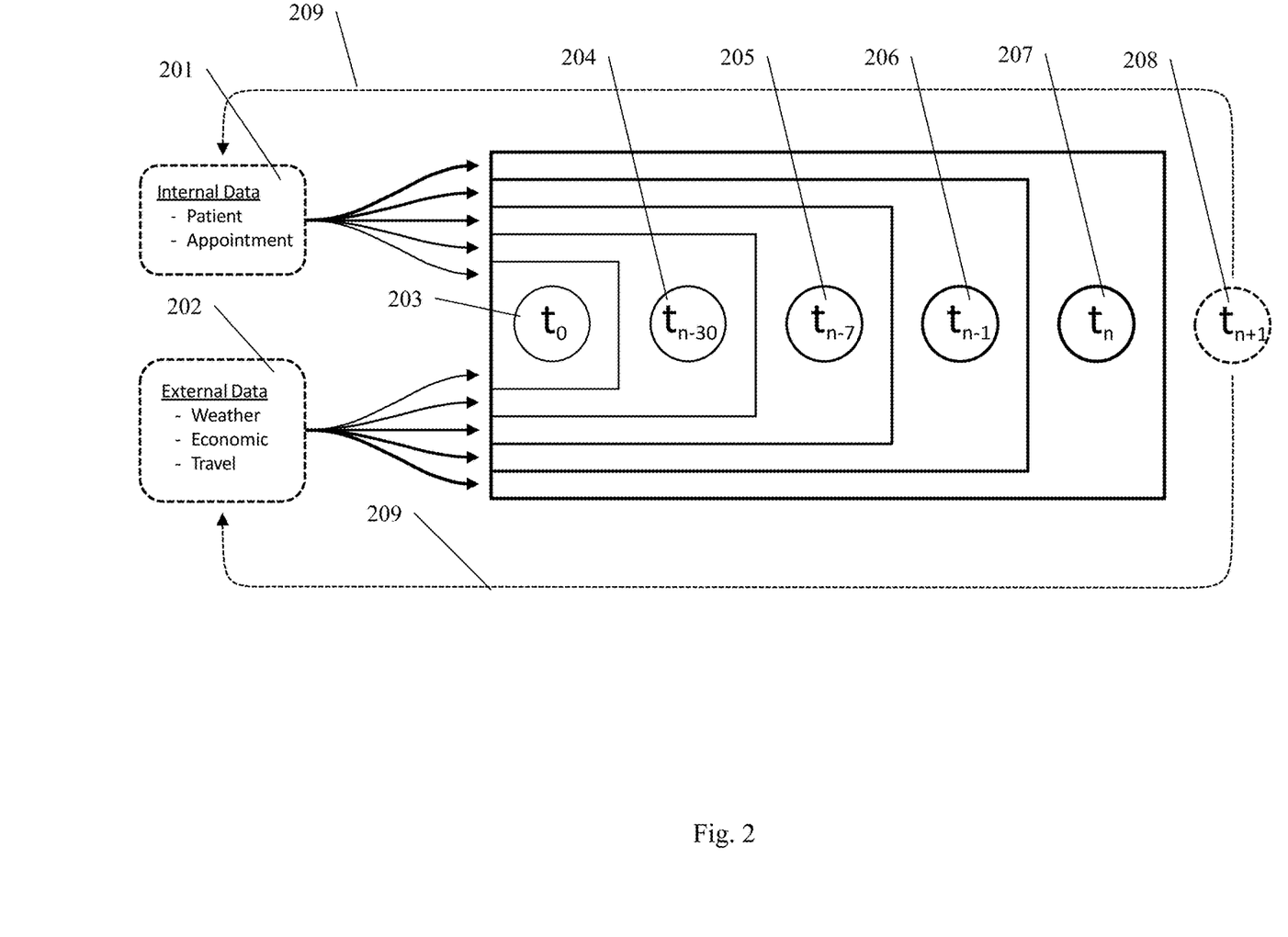
FIG. 2 is a diagram of a machine learning model of the disclosed system.

With reference to FIG. 2, an exemplary diagram of a machine learning model of the disclosed system is shown. The depicted model comprises internal data 201 and external data 202 as inputs, as described in further detail above. Inferences are made at a set of time indices before the appointment, for example at to (the date that the appointment is made and/or confirmed, 203) at $t_{n-30}$ (30 days before the day of the appointment, 204), $t_{n-7}$ (one week before the day of the appointment, 205) $t_{n-1}$ (one day before the day of the appointment, 206), and $t_n$ (on the day of the appointment, 207). In some embodiments, inferences may also be made on $t_{n+1}$ (the day after the appointment, 208) and some or all of the inferences, along with the actual outcome of the appointment as known on $t_{n+1}$, may be fed back into the machine learning model via a feedback path 209.

Although various example sets of time windows are presented in different examples herein, it is understood that a system as disclosed may use any suitable time windows to infer attendance probability, including but not limited to one year prior, eleven months prior, ten months prior, nine months prior, eight months prior, seven months prior, six months prior, five months prior, four months prior, three months prior, two months prior, one month prior, six weeks prior, five weeks prior, four weeks prior, three weeks prior, two weeks prior, one week prior, six days prior, five days prior, four days prior, three days prior, two days prior, one day prior, 36 hours prior, twelve hours prior, eleven hours prior, ten hours prior, nine hours prior, eight hours prior, seven hours prior, six hours prior, five hours prior, four hours prior, three hours prior, two hours prior, one hour prior, etc. In some embodiments, a time window may be chosen based on an estimated travel time from the attendee's residence or place of business and the provider. For example, where an expected travel time for an attendee, with traffic, is one hour, an attendance probability may be inferred ninety minutes prior to the appointment based in part on current weather conditions and traffic data, and a mitigation step may be taken to improve the attendance probability (for example sending a text message or other communication to the attendee to remind them of their upcoming appointment and advise that they leave soon).

As discussed above, the disclosed model includes external information gathered at the time of the appointment or at the time of the inference, which helps gain an understanding of the ways that an attendee may approach decision making when deciding on whether to seek/participate in an appointment.

Mitigation Component

The system may further comprise a mitigation component, configured to respond to various ranges of attendance probability at various times prior to an upcoming appointment by automatically providing to the attendee (or suggesting to a user or provider) one or more mitigation strategies designed to increase the probability of attendance at the appointment. Depending on a value of a calculated attendance probability, one or more of the below-identified mitigation strategies may be used. In some scenarios, a first mitigation strategy may be applied at a first time index prior to the appointment time, for example seven days before the appointment, and a second mitigation strategy may be applied at a second time index prior to the appointment time, for example one day before the appointment. In some embodiments, the first and second mitigation strategies may both be determined from a single attendance probability prediction, and in other embodiments, the second mitigation strategy may be applied as a result of a second, updated calculation of an attendance probability after application of the first mitigation strategy.

The models disclosed herein may weight variables differently on their predictive power at different time indices prior to the appointment. The models may also weight variables differently on their predictive power based on other variables. For example, in some embodiments, poor weather may be considered more significant for attendees of advanced age. As discussed in further detail below, in some embodiments different variable weights may be tuned based on attendee feedback gathered both before the appointment (e.g. asking the attendee for their preferred communication/transportation method) and/or after the appointment (e.g. asking the attendee to suggest, after a missed appointment, what if anything could have been done so that they attended the appointment).

Transportation-based mitigation strategies may include providing personalized maps to the attendee or providing specific directions to the attendee, for example from the attendee's home or place of business to the provider. Other options include provision of a ride-sharing or taxi ride to pick the attendee up and take them to the provider, or to provide guidance to and/or fare payment for public transportation, for example a bus, subway, or train. In some embodiments, transportation-based mitigation may include provision of other automotive transportation, for example a car, ambulance, or ambulette. In some embodiments, a transportation-based strategy may include providing information or training to one or more personnel of a transportation method provided, for example training or refreshing on particular diseases or symptoms to a clinician dispatched in a form of automotive transportation, for example an ambulance. In some embodiments, transportation-based mitigation may comprise personal outreach in the home or office or, in a medical implementation, referring an attendee/patient to home-based care.

Communication-based mitigation strategies include, but are not limited to, written communication, telephonic communication—for example cell phone calls, land line calls, or text messages, personal outreach, EMS outreach, or EMR outreach (e.g. messages transmitted via a patient-facing EMR). In some embodiments, communication may be indirect, for example an electronic advertisement via social media and/or search engine. The nature of the communication can vary depending on the circumstances and the medium. In some embodiments, the communication may be a direct, simple reminder, but in other embodiments the communication may be a survey or a series of questions or a screening questionnaire, or, for example, a personalized checklist of factors to discuss with the attendee. In one example, an attendee may be told that there are some number of common factors that often influence poor attendance, and the attendee may then be asked to suggest ways the provider or a third party may help the attendee to overcome these factors. In some embodiments, a communication-based mitigation strategy may be simply to move the appointment to a telemedicine or other virtual visit, for example by providing the attendee with a tablet or mobile computing device preconfigured to facilitate the virtual visit.

A sub-component of the mitigation component is a follow-up component after an appointment has been missed or successfully completed. A follow-up may comprise surveys, text messages, phone calls, or personal outreach directed to gathering information for use on predicting future appointment attendance. An attendee may be asked for example what reason or reasons they had for missing an appointment, or may be asked to provide feedback on one or more mitigation strategies applied by the provider. An attendee may be asked to provide ideas for increasing the ease of attending the appointment, providing preferences regarding future appointment types, to list challenges they face in attending appointments with this or other providers, and/or related questions, including but not limited to medical questions. An attendee may also be asked more general questions related to the appointment itself, for example, in a medical appointment, how well the attendee thinks a clinician treated their issue, how well their clinician listened, their opinion of a nurse or ancillary service provider, whether a referred provider was convenient to them, etc.

Figure 3:
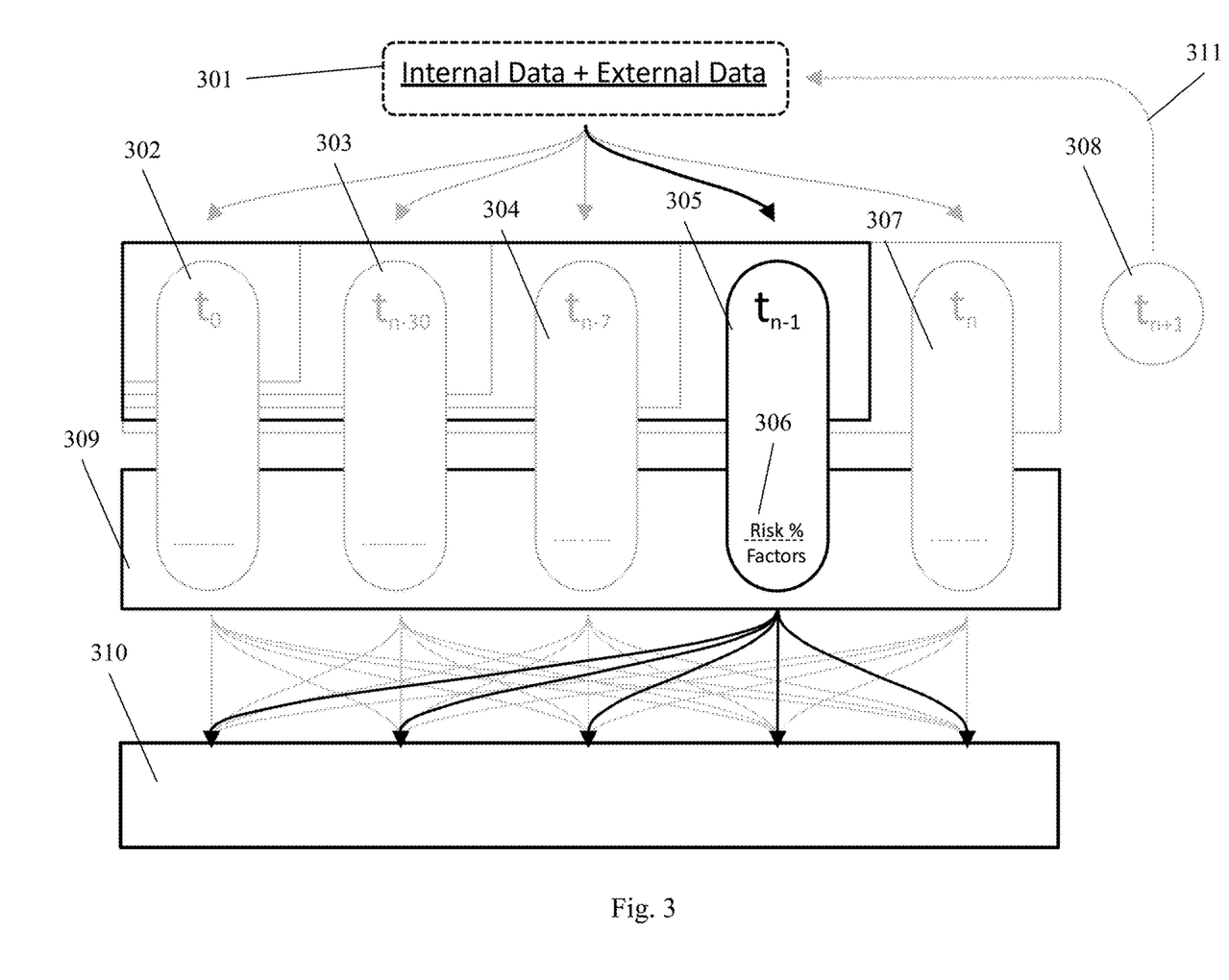
FIG. 3 is a system-level diagram of a system for improving appointment attendance.

A diagram of an overall system including mitigation strategies is shown in FIG. 3, which is structured similarly to the diagram of FIG. 2. As shown in FIG. 3, the system comprises one or more databases 301 comprising external data, population data, and appointment data. Inferences are made about a given appointment at a set of time indices before the appointment, for example at to (the date that the appointment is made and/or confirmed, 302) at $t_{n-30}$ (30 days before the day of the appointment, 303), $t_{n-7}$ (one week before the day of the appointment, 304) $t_{n-1}$ (one day before the day of the appointment, 305), and to (on the day of the appointment, 307). In some embodiments, inferences may also be made on $t_{n+1}$ (the day after the appointment, 308) and some or all of the inferences, along with the actual outcome of the appointment as known on $t_{n+1}$, may be fed back into the machine learning model via a feedback path 311.

At some or all of the time windows, a probability of one or more risk factors 306 may be calculated, and the probability may be used to schedule or suggest one or more mitigation steps 310 at one or more of the time windows. In one example, an appointment having a low attendance probability calculated at time window 303 (30 days prior to the appointment) may result in a mitigation step being scheduled for time window 304 (seven days prior to the appointment).

The disclosed systems and methods may comprise any of the below numbered embodiments.

Embodiment 1—A computer-implemented method of increasing appointment attendance, comprising: providing at least one processor; and at least one non-transitory memory including computer program code for one or more programs, the at least one non-transitory memory and the computer program code configured to, with the at least one processor, perform steps comprising: obtaining an appointment data structure, comprising an attendee and a corresponding appointment for the attendee; obtaining a set of population data related to the attendee; obtaining a set of appointment data related to the appointment; obtaining a set of external data; obtaining environmental data related to the region around a location of the appointment or the attendee at a designated time; inferring, using the population data, the appointment data, the external data, and the environmental data in a machine learning algorithm by the at least one processor and the at least one non-transitory memory, a probability that the attendee will attend the appointment; and when the probability of attendance is below a threshold, performing a mitigation step to increase the probability that the attendee will attend the appointment.

Embodiment 2— the method of embodiment 1, wherein the designated time is at least one day prior to a date of the appointment.

Embodiment 3—The method of embodiments 1 or 2, wherein the designated time is selected from at least one month prior to the date of the appointment, at least one week prior to the date of the appointment, at least three days prior to the day of the appointment, or at least one day prior to the date of the appointment.

Embodiment 4—The method of any of embodiments 1-3, wherein the environmental data comprises weather data.

Embodiment 5—The method of any of embodiments 1-4, wherein the external data comprises economic data.

Embodiment 6—The method of any of embodiments 1-5, wherein the economic data comprises economic data related to the region around the attendee.

Embodiment 7—The method of any of embodiments 1-6, wherein the economic data comprises global or national economic data.

Embodiment 8—The method of any of embodiments 1-7, further comprising the step of inferring a communication preference of the attendee.

Embodiment 9—The method of any of embodiments 1-8, wherein the mitigation step comprises a communication step selected from written, telephonic, text message, or electronic mail communication based on the inferred communication preference of the attendee.

Embodiment 10—The method of any of embodiments 1-9, wherein the mitigation step comprises providing transportation assistance to the attendee, the transportation assistance selected from transportation maps, a ride sharing credit, a public transportation credit, or an ambulance dispatch.

Embodiment 11—The method of any of embodiments 1-10, wherein the mitigation step comprises converting the appointment to a virtual appointment or changing a location of the appointment to a home or place of business of the attendee.

Embodiment 12—The method of any of embodiments 1-11, wherein the appointment data comprises data selected from a provider of the appointment, a nature of the appointment, whether the appointment is related to a cancer, one or more conditions the attendee holds, one or more diagnoses the attendee is currently being treated for, whether the appointment is telemedicine or in-person, or whether the appointment is an initial consultation or a second opinion.

Embodiment 13—A computer-implemented method of increasing appointment attendance, comprising: providing at least one processor; and at least one non-transitory memory including computer program code for one or more programs, the at least one non-transitory memory and the computer program code configured to, with the at least one processor, perform steps comprising: obtaining a pending appointment data structure comprising an attendee and a corresponding appointment for the attendee; obtaining a set of electronic medical record (EMR) data related to the attendee; obtaining a set of appointment data related to the appointment; obtaining a set of past appointment data structures, each comprising an attendee identity, a past appointment, and an attendance status of the past appointment; obtaining a set of external data related to the attendees in the set of past appointment data structures; obtaining a set of regional environmental data related to a region around a location of the appointment or the attendees in the set of past appointment data structures from a time of each past appointment; training a machine learning model with the set of past appointment data structures, the set of external data, and the set of environmental data; obtaining environmental data related to the region around the location of the appointment or the attendee in the pending appointment data structure at a designated time; inferring, using the machine learning algorithm, a probability that the attendee will attend the appointment; and when the probability of attendance is below a threshold, performing a mitigation step to increase the probability that each attendee will attend each corresponding appointment.

Embodiment 14—The method of embodiment 13, further comprising the step of: after the appointment in the pending appointment data structure has passed, recording an attendance status of the attendee at the appointment; and further training the machine learning model with the pending appointment data structure and the attendance status.

Embodiment 15—The method of embodiment 13 or 14, wherein the environmental data and the regional environmental data comprise weather data.

Embodiment 16—The method of any of embodiments 13-15, further comprising the step of inferring whether a mobility factor selected from age, disability status, or travel time is contributive above a predetermined threshold.

Embodiment 17—The method of any of embodiments 13-16, wherein the mitigation step comprises providing transportation assistance to the attendee, the transportation assistance selected from transportation maps, a ride sharing credit, a public transportation credit, an ambulance dispatch, or an ambulette dispatch when the mobility factor is above the predetermined threshold.

Embodiment 18—The method of any of embodiments 13-17, wherein the attendance status of the past appointment in the appointment data structures is selected from attending, no-show, late, rescheduled, converted to telemedicine, or cancelled surgery.

Embodiment 19—The method of any of embodiments 13-18, wherein the machine learning algorithm is a random forest.

Embodiment 20—The method of any of embodiments 13-19, wherein the method further comprises the steps of: obtaining the set of EMR data in at least two different data formats; and standardizing the at least two different data formats before training the machine learning model with the EMR data.

Embodiment 21—A system for increasing appointment attendance, comprising: a non-transitory computer-readable storage medium with instructions stored thereon, which when executed by a processor, perform steps comprising: obtaining an appointment data structure, comprising an attendee and a corresponding appointment for the attendee; obtaining a set of electronic medical record (EMR) data related to the attendee; obtaining a set of data related to the appointment; obtaining a set of external data; obtaining environmental data related to the region around a location of the appointment or the attendee at a designated time; inferring, using the EMR data, data related to the appointment, external data, and environmental data in a machine learning algorithm, a probability that the attendee will attend the appointment; and when the probability of attendance is below a threshold, recommending a mitigation step to increase the probability that the attendee will attend the appointment.

Embodiment 22—The system of embodiment 21, further comprising inferring the probability that the attendee will attend the appointment using a trained machine learning algorithm executed on the processor.

Embodiment 23—The system of embodiment 21 or 22, wherein the non-transitory computer-readable medium further comprises at least a portion of the database of an EMR system comprising the EMR data.

Embodiment 24—The system of any of embodiments 21-23, the instructions further comprising performing the mitigation step, the mitigation step comprising sending one computer-generated electronic communication message to the attendee.

Embodiment 25—A non-transitory computer-readable storage medium having stored thereon one or more program instructions which, when executed by one or more processors, cause an apparatus to at least perform the following operations: obtain an appointment data structure, comprising an attendee and a corresponding appointment for the attendee; obtain a set of population data related to the attendee; obtain a set of appointment data related to the appointment; obtain a set of external data; obtain environmental data related to the region around a location of the appointment or the attendee at a designated time; infer, using the population data, appointment data, external data, and environmental data in a machine learning algorithm, a probability that the attendee will attend the appointment; and when the probability of attendance is below a threshold, recommending a mitigation step to increase the probability that the attendee will attend the appointment.

Embodiment 26—The non-transitory computer readable storage medium of embodiment 25, further comprising at least one database including at least a subset of the population data, the appointment data, the external data, and the environmental data stored thereon.

Embodiment 27—The non-transitory computer-readable storage medium of embodiment 25 or 26, wherein the set of population data comprises electronic medical record (EMR) data.

Embodiment 28—The non-transitory computer-readable storage medium of any of embodiments 25-27, the program instructions further configured to cause the apparatus to perform at least part of the mitigation step via an automated process.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

REFERENCES

The following publications are incorporated herein by reference in their entirety:

Liu, D., Shin, WY., Sprecher, E. et al. Machine learning approaches to predicting no-shows in pediatric medical appointment. *npj Digit. Med.* 5, 50 (2022). https://doi.org/10.1038/s41746-022-00594-w

What is claimed is:

1. A computer-implemented method of increasing appointment attendance, comprising:
 providing at least one processor; and at least one non-transitory memory including computer program code for one or more programs, the at least one non-transitory memory and the computer program code configured to, with the at least one processor, perform steps comprising:
 obtaining an appointment data structure, comprising an attendee and a corresponding appointment for the attendee;
 obtaining a set of electronic medical record (EMR) data related to the attendee, wherein the set of EMR data is in at least two different formats;
 standardizing the at least two different formats of the set of EMR data;
 at a first time:
  obtaining a set of population data related to the attendee;
  obtaining a set of appointment data related to the appointment;
  obtaining a set of external data;
  obtaining environmental data related to the region around a location of the appointment or the attendee at the first time;
  inferring, using the standardized EMIR data, the population data, the appointment data, the external data, and the environmental data in a machine learning algorithm by the at least one processor and the at least one non-transitory memory, a probability that the attendee will attend the appointment; and
  when the probability of attendance is below a threshold, performing a mitigation step selected from a first group of mitigation steps to increase the probability that the attendee will attend the appointment;
 at a second time after the first time:
  obtaining a second set of population data related to the attendee;
  obtaining a second set of appointment data related to the appointment;
  obtaining a second set of external data;
  obtaining environmental data related to the region around a location of the appointment or the attendee at the second time;
  inferring, using the standardized EMR data, the second set of population data, the second set of appointment data, the second set of external data, and the environmental data in the machine learning algorithm by the at least one processor and the at least one non-transitory memory, a probability that the attendee will attend the appointment; and
  when the probability of attendance is below a threshold, performing a mitigation step selected from a second group of mitigation steps different from the first group of mitigation steps, to increase the second probability that the attendee will attend the appointment.

2. The method of claim 1, wherein the first time is at least one day prior to a date of the appointment.

3. The method of claim 2, wherein the first time is selected from at least one month prior to the date of the appointment, at least one week prior to the date of the appointment, or at least three days prior to the day of the appointment.

4. The method of claim 1, wherein the environmental data comprises weather data.

5. The method of claim 1, wherein the external data comprises economic data.

6. The method of claim 5, wherein the economic data comprises economic data related to the region around the attendee.

7. The method of claim 5, wherein the economic data comprises global or national economic data.

8. The method of claim 1, further comprising the step of inferring a communication preference of the attendee.

9. The method of claim 8, wherein the first mitigation step comprises a communication step selected from written, telephonic, text message, or electronic mail communication based on the inferred communication preference of the attendee.

10. The method of claim 1, wherein the first mitigation step comprises providing transportation assistance to the attendee, the transportation assistance selected from transportation maps, a ride sharing credit, a public transportation credit, or an ambulance dispatch.

11. The method of claim 1, wherein the first mitigation step comprises converting the appointment to a virtual appointment or changing a location of the appointment to a home or place of business of the attendee.

12. The method of claim 1, wherein the appointment data comprises data selected from a provider of the appointment, a nature of the appointment, whether the appointment is related to a cancer, one or more conditions the attendee holds, one or more diagnoses the attendee is currently being treated for, whether the appointment is telemedicine or in-person, or whether the appointment is an initial consultation or a second opinion.

13. A computer-implemented method of increasing appointment attendance, comprising:
 providing at least one processor; and at least one non-transitory memory including computer program code for one or more programs, the at least one non-transitory memory and the computer program code configured to, with the at least one processor, perform steps comprising:
 obtaining a set of electronic medical record (EMR) data related to an attendee in at least two different data formats;
 standardizing the at least two different data formats of the set of EMR data;
 obtaining a set of past appointment data structures, each comprising an attendee identity, a past appointment, and an attendance status of the past appointment;
 obtaining a set of external data related to the attendees in the set of past appointment data structures;
 obtaining a set of regional environmental data related to a region around a location of the appointment or the attendees in the set of past appointment data structures from a time of each past appointment;
 training a machine learning algorithm with the standardized EMR data, the set of past appointment data structures, the set of external data, and the set of environmental data;
 at a first time:
  obtaining a pending appointment data structure comprising the attendee and a corresponding appointment for the attendee;
  obtaining a set of appointment data related to the appointment;

obtaining environmental data related to the region around the location of the appointment or the attendee in the pending appointment data structure at the first time;
inferring, using the trained machine learning algorithm, a probability that the attendee will attend the appointment; and
when the probability of attendance is below a threshold, performing a first mitigation step selected from a first group of mitigation steps to increase the probability that the attendee will attend the appointment;
at a second time after the first time:
obtaining the pending appointment data structure comprising the attendee and the corresponding appointment for the attendee;
obtaining a set of appointment data related to the appointment;
obtaining second environmental data related to the region around the location of the appointment or the attendee in the pending appointment data structure at the second time;
inferring, using the trained machine learning algorithm, a second probability that the attendee will attend the appointment; and
when the second probability of attendance is below a second threshold, performing a second mitigation step selected from a second group of mitigation steps different from the first group of mitigation steps, to increase the probability that the attendee will attend the appointment.

14. The method of claim 13, further comprising the steps of:
after the appointment in the pending appointment data structure has passed, recording an attendance status of the attendee at the appointment; and
further training the machine learning algorithm with the pending appointment data structure and the attendance status.

15. The method of claim 13, wherein the environmental data and the regional environmental data comprise weather data.

16. The method of claim 13, further comprising the step of inferring whether a mobility factor selected from age, disability status, or travel time is contributive above a predetermined threshold.

17. The method of claim 16, wherein the first mitigation step comprises providing transportation assistance to the attendee, the transportation assistance selected from transportation maps, a ride sharing credit, a public transportation credit, an ambulance dispatch, or an ambulette dispatch when the mobility factor is above the predetermined threshold.

18. The method of claim 14, wherein the attendance status of the past appointment in the appointment data structures is selected from attending, no-show, late, rescheduled, converted to telemedicine, or cancelled surgery.

19. The method of claim 13, wherein the machine learning algorithm is a random forest.

20. A system for increasing appointment attendance, comprising:
a non-transitory computer-readable storage medium with instructions stored thereon, which when executed by a processor, perform steps comprising:
obtaining an appointment data structure, comprising an attendee and a corresponding appointment for the attendee;
obtaining a set of electronic medical record (EMR) data in at least two different formats related to the attendee;
standardizing the at least two different formats of the set of EMR data;
at a first time:
obtaining a first set of data related to the appointment;
obtaining a first set of external data;
obtaining first environmental data related to the region around a location of the appointment or the attendee at the first time;
inferring, using the standardized EMR data, the first set of data related to the appointment, the first set of external data, and the first environmental data in a machine learning algorithm, a first probability that the attendee will attend the appointment; and
when the first probability of attendance is below a first threshold, recommending a first mitigation step selected from a first group of mitigation steps to increase the probability that the attendee will attend the appointment at a second time after the first time:
obtaining a second set of data related to the appointment;
obtaining a second set of external data;
obtaining second environmental data related to the region around a location of the appointment or the attendee at the second time;
inferring, using the standardized EMR data, the second set of data related to the appointment, the second set of external data, and the second environmental data in the machine learning algorithm, a second probability that the attendee will attend the appointment; and
when the second probability of attendance is below a second threshold, recommending a second mitigation step selected from a second group of mitigation steps different from the first group of mitigation steps to increase the probability that the attendee will attend the appointment.

21. The system of claim 20, the instructions further comprising inferring the first probability that the attendee will attend the appointment using a trained machine learning algorithm executed on the processor.

22. The system of claim 20, wherein the non-transitory computer-readable medium further comprises at least a portion of the database of an EMR system comprising the EMR data.

23. The system of claim 20, the instructions further comprising performing the first mitigation step, the first mitigation step comprising sending one computer-generated electronic communication message to the attendee.

24. A non-transitory computer-readable storage medium having stored thereon one or more program instructions which, when executed by one or more processors, cause an apparatus to at least perform the following operations:
obtain an appointment data structure, comprising an attendee and a corresponding appointment for the attendee;
obtain a set of electronic medical record (EMR) data related to the attendee, wherein the set of EMR data is in at least two different formats;
standardize the at least two different formats of the set of EMR data;

at a first time:
- obtain a first set of population data related to the attendee;
- obtain a first set of appointment data related to the appointment;
- obtain a first set of external data;
- obtain first environmental data related to the region around a location of the appointment or the attendee at first time;
- infer, using the standardized EMR data, the first set of population data, the first set of appointment data, the first set of external data, and the first environmental data in a machine learning algorithm, a first probability that the attendee will attend the appointment; and
- when the first probability of attendance is below a first threshold, recommending a first mitigation step selected from a first group of mitigation steps to increase the probability that the attendee will attend the appointment, at a second time after the first time:
- obtain a second set of population data related to the attendee;
- obtain a second set of appointment data related to the appointment;
- obtain a second set of external data;
- obtain second environmental data related to the region around a location of the appointment or the attendee at the second time;
- infer, using the standardized EMR data, the second set of population data, the second set of appointment data, the second set of external data, and the second environmental data in the machine learning algorithm, a second probability that the attendee will attend the appointment; and
- when the second probability of attendance is below a second threshold, recommending a second mitigation step selected from a second group of mitigation steps different from the first group of mitigation steps to increase the probability that the attendee will attend the appointment.

25. The non-transitory computer readable storage medium of claim 24, further comprising at least one database including at least a subset of the first set of population data, the first set of appointment data, the first set of external data, and the first environmental data stored thereon.

26. The non-transitory computer-readable storage medium of claim 24, the program instructions further configured to cause the apparatus to perform at least part of the first or second mitigation step via an automated process.

* * * * *